_US005490985A_

United States Patent [19]

Wallach et al.

[11] Patent Number: 5,490,985
[45] Date of Patent: Feb. 13, 1996

[54] EXTENDED DURATION ANTACID PRODUCT

[75] Inventors: Donald F. H. Wallach, Hollis, N.H.; Rajiv Mathur, Sewell, N.J.; Jean Philippot, St. Clement la Riviere, France; Surendra Kumar, Vineland, N.J.

[73] Assignee: Micro-Pak, Inc., Wilmington, Del.

[21] Appl. No.: 210,645

[22] Filed: Mar. 18, 1994

Related U.S. Application Data

[63] Continuation of Ser. No. 984,895, Dec. 2, 1992, abandoned.

[51] Int. Cl.$^6$ ............ A61K 9/127; A61K 33/12; A61K 33/06; A61K 33/10; A61K 31/695
[52] U.S. Cl. ............ 424/450; 424/683; 424/684; 424/686; 424/690; 514/63
[58] Field of Search ............ 424/450, 683, 424/684, 686, 690; 514/63

[56] References Cited

U.S. PATENT DOCUMENTS

| | | | |
|---|---|---|---|
| 4,839,175 | 6/1989 | Guo et al. | 424/450 |
| 4,895,452 | 1/1990 | Yiounas et al. | 366/173 |
| 4,911,928 | 3/1990 | Wallach | 424/450 |
| 5,013,497 | 5/1991 | Yiournas et al. | 264/4.1 |
| 5,032,457 | 7/1991 | Wallach | 428/402.2 |
| 5,147,723 | 9/1992 | Wallach | 428/402.2 |
| 5,164,191 | 11/1992 | Tabibi et al. | 424/450 |
| 5,192,549 | 3/1993 | Barenolz et al. | 424/450 |
| 5,230,899 | 7/1993 | Park et al. | 424/450 |
| 5,260,065 | 11/1993 | Mathur et al. | 424/450 |

Primary Examiner—Marianne M. Cintins
Assistant Examiner—William R. A. Jarvis
Attorney, Agent, or Firm—Lahive & Cockfield

[57] ABSTRACT

An antacid product having extended duration of residence in the gastric and upper intestinal systems has been developed. This antacid product includes a blend of 10–70% by volume nonphospholipid lipid vesicles, with a particulate base. An antiflatulence agent may also be included. A method of providing extended duration amelioration of acid build up in the gastric and upper intestinal tract using this product is also disclosed.

30 Claims, No Drawings

EXTENDED DURATION ANTACID PRODUCT

This application is a continuation of application Ser. No. 07/984,895, filed on Dec. 2, 1992, now abandoned.

BACKGROUND OF THE INVENTION

As the population has grown older due to improvement in health conditions, one of the attendant consequences is that stomach problems which plague many older people are more prevalent. Normally, the problem is simple heartburn caused by excess stomach acid and gas. The same effect often occurs from the frenetic pace of modern life. The over-the-counter or OTC market is filled with antacid preparations to ameliorate this problem. These preparations normally include bases in the form of metal hydroxides, metal carbonates and bicarbonates and metal hydrosilicates which act as buffering agents for the excess stomach acid. Commonly used metals are aluminum, calcium, magnesium and in some instances sodium. However, the multivalent ions are more commonly used because too much sodium can be dangerous for those with some form of heart condition.

The metal bases are normally in the form of relatively large particles or particulates which form a colloid or suspension in an aqueous carrier. The antacid may also include other additives such as an antiflatulence agent to minimize gas buildup as well as some form of flavoring to make the mixture more palatable.

While the antacid preparations available in the OTC market are fairly effective at the requisite buffering action, many people must take these antacid preparations several times a day because the duration of effectiveness is fairly short. In fact, although the manufacturers will normally recommend that these preparations will be taken no more than four times a day because of metal ion toxicity, the actual duration of effectiveness of each dose in the gastric and upper intestinal system is in the order of forty-five minutes to an hour, after which the antacids are cleared. In order to counteract this clearing problem, several manufacturers have gone to the so-called "extra-strength" products which merely double the amount of base in the antacid product. The theory behind these extra strength products is that even as most of the base is cleared from the effective zone, the residual amount will have sufficient buffering strength to at least partially ameliorate the acid build-up problem. However, no one has previously developed a way of keeping a significant amount of base in the active gastric and upper intestinal systems for a longer duration.

The present invention solves this extended duration problem with the use of lipid vesicles as an integral part of the antacid product. While lipid vesicles, particularly the phospholipid vesicles called liposomes, have been discussed for use in a variety of pharmaceutical, cosmetic and personal care products, they are normally not considered for enteral use because liposomes, being made of phospholipids, are readily hydrolysed by both phospholipases and acid lipases. The gastrointestinal intestinal tract is replete with these lipases and phospholipid vesicles break down much too quickly to be of any real use. Although there are acid stabilized phospholipids which have been made into vesicles (see U.S. Pat. No. 4,221,732), these have not been used for a commercial OTC enteral product for cost reasons. Phospholipids which are sufficiently pure for an enteral product are expensive, costing hundreds of dollars per kilogram, and the acid stabilized phospholipids are even more expensive. Accordingly, although it may be feasible to make enteral products having vesicles which are acid stable so that they can be used in the gastrointestinal tract, it is not economically practical.

However, changes in lipid vesicle technology in the last few years are now making it possible to use lipid vesicles in OTC products. The reason is that a variety of new materials have been successfully tried as vesicle formers in place of phospholipids. U.S. Pat. Nos. 4,911,928, 5,147,723, and 5,032,457 and well as U.S. patent application Ser. No. 761,253, the disclosures of which are incorporated herein by reference, all show much less expensive materials which can be made successfully into vesicles. In addition, vesicle making procedures are also being modified to use faster, more cost efficient methods. U.S. Pat. Nos. 4,895,452 and 5,013,497, the disclosures of which are also incorporated herein by reference, describe apparatus and methods for rapid vesicle formation whereby the lipid vesicles are formed in milliseconds with throughparts in the ? liter/hour range. The ability to form vesicles in this high volume mode, coupled with the use of less expensive materials, has finally brought the price of lipid vesicles into the region it is economically feasible for OTC enteral products. In addition, since these new materials are not phospholipids they are not subject to degradation by phospholipases. Selected materials are also not subject to the acid lipases. As such, they can provide the vesicles which have long term stability in the gastrointestinal tract.

Accordingly, it is an object of the invention to provide an antacid product having extended duration in the gastric and upper intestinal systems.

Another object of the invention is to provide an antacid product which includes lipid vesicles.

A further object of the invention is to provide a method of extending the duration or residence time of actives from an antacid in the gastric and upper intestinal tract.

These and other objects and features of the invention will be apparent from the following description.

SUMMARY OF THE INVENTION

The present invention features an antacid product having extended lifetime or duration of residence in the gastric and upper intestinal systems. The invention further features a method of ameliorating acid build-up in the gastric and upper intestinal tracts using the product of the invention.

The antacid product of the invention comprises a mixture of lipid vesicles and an aqueous solution of a particulate base, with the lipid vesicles forming 10–70% by volume. The mixture may be in the form of a colloid, a suspension, or may even be dried by means such as lyophilization or sprayed drying to form a dried product. While phospholipid lipid vesicles (or liposomes) may be used, preferably they should be made from acid stabilized phospholipids. However, nonphospholipid lipid vesicles are preferred.

The particulate base is preferably a metal hydroxide, a metal hydrosilicate, a metal carbonate or bicarbonate, or some mixture thereof. The term "particulate", as used herein, means that the base is not entirely dissolved in the aqueous carrier solution but rather has a distinct form. In most circumstances, the particulate base will be an aggregate of many particles of the base, forming a particulate in the cubic micron or larger range. The preferred metal ions for use in the bases are sodium, calcium, aluminum and magnesium, most preferably one of the multivalent cations.

Often, a mixture of bases, e.g., aluminum hydroxide and magnesium hydroxide, are used.

The antacid product may also contain an antiflatulence agent such as a silicone oil. A preferred silicone oil for this purpose is simethicone. The antiflatulence agent may be exterior to the vesicles or, in some circumstances, carried in the vesicles. Paucilamellar lipid vesicles, which may have a large amorphous central cavity that can be filled with an oily material such as a silicone oil, are particularly advantageous for carrying the oil. This allows the oil to be entrapped until breakdown of the vesicles in the lower intestinal tract, the primary site of activity for this antiflatulence agent.

If nonphospholipid materials are used as the primary vesicle formers, a broad variety of materials could be used. One preferred class of materials is selected from the group consisting of:

diethanolamides having the formula $$(HOCH_2-CH_2)_2NCO-R_3$$

where $R_3$ is a radical of caprylic, lauric, myristic or linoleic acids;

long chain acyl hexosamides having the formula $$R_4-NHCO-(CH_2)_b-CH_3$$

where b ranges from 10–18 and $R_4$ is a radical of a sugar molecule selected from a group consisting of glucosamine, galactosamine, and N-methylglucamine; and long chain acyl amino acid amides having the formula $$R_5-CH(COOH)-NHCO-(CH_2)_c-CH_3$$

where c ranges from 10–18 and $R_5$ is a radical of an amino acid side chain;

long chain acyl amides having the formula $$HOOC-(CH_2)_d-N(CH_3)-(CH_2)_3-NHCO-R_6$$

where $R_6$ is an acyl chain having 12–20 carbons and not more than two unsaturations, and d ranges from 1—3; and glycerol monostearate.

A second grouping of preferred materials consists of:

polyoxyethylene fatty esters having the formula $$R_1-COO(C_2H_4O)_nH$$

where $R_1$ is a radical of lauric, myristic, cetyl, stearic, or oleic acid and n=2–10;

polyoxyethylene fatty acid ethers, having the formula $$R_2-CO(C_2H_4O)_mH$$

where $R_2$ is a radical of lauric, myristic, or cetyl acids, single or double unsaturated octadecyl acids, or double unsaturated eicosadienoic acids and m ranges from 2–4;

polyoxyethylene (20) sorbitan mono- or trioleate; and polyoxyethylene glyceryl monostearate with 1–10 polyoxyethylene groups.

Another preferred group of materials for vesicle formation are the betaines and sarcosinamides.

Still another type of nonphospholipid vesicle which may be used in the present antacid product requires a blend of two distinct lipids, a primary lipid and a secondary lipid. The primary lipid, which forms the greatest proportion by weight of any lipid and is preferably 50% or higher by weight of lipid in the vesicle, should be selected from the group consisting of $C_{12}$–$C_{18}$ fatty alcohols, $C_{12}$–$C_{18}$ glycol monoesters, $C_{12}$–$C_{18}$ glyceryl mono-and diesters, and mixtures thereof. The secondary lipid must be present in an amount sufficient to allow formation of the lipid vesicles, and is selected from the group consisting of quaternary dimethyldiacyl amines, polyoxyethylene acyl alcohols, polyglycerols, sorbitan fatty acid esters, fatty acids and their salts, and mixtures thereof.

Many of these materials are found in food products, and, as such, are well digested by the body in the intestinal tract.

The lipid vesicles may also include either a positive or negative charge producing agent. If a positive charge producing agent is used, it is preferably selected from the group consisting of long chain amines, long-chain pyridinium compounds, quaternary ammonium compounds and mixtures thereof. A most preferred positive charge producing agent is cetyl pyridinium chloride. If a negative charge producing agent is used, it is preferably selected from the group of consisting of dicetyl phosphate, cetyl stearate, phosphatidic acid, phosphatidylserine, oleic acid, palmitic acid and mixtures thereof. The vesicle may also include a sterol such as cholesterol, phytosterol, hydrocortisone, or some mixture thereof.

The method of the invention, which is useful in ameliorating acid build up in the gastric and upper intestinal systems, has the step of administering an effective amount of the antacid product previously described which has extended residence in the gastrointestinal tract. While the exact mechanism for this extended residence is not known, it is theorized that it is based on an aggregation between the particulate base and the vesicles. Since the vesicles themselves have extended duration of residence in the gastric and upper intestinal systems, the aggregated product should have a similar extended duration. One hypothesis is that the vesicles bind or are entrapped by the gastric and upper intestinal mucosa, thereby extending their residence time in the gastric and upper intestinal system. However, the scientific reason for this extended duration is not necessary for understanding the purposes of the invention.

DETAILED DESCRIPTION OF THE INVENTION

The antacid product of the invention is effective in providing extended duration acid buffering in the gastric and upper intestinal tract. Dosage is comparable to traditional antacid products, which vary from person-by-person with two to four teaspoons every four hours and a maximum of about twelve teaspoons daily recommended. Each teaspoon is approximately 5 ml and includes about 100–500 mg of the base and if present, 10–25 mg of an antiflatulence agent. The antacid mixture may also include stabilizing agents such as butyl and propyl paraben; thickeners such as carboxymethylcellulose, hydroxyproplymethylcellulose, and microcrystalline cellulose; sodium, flavoring, and sorbitol in addition to the particulate base. These materials are similar to antacid products without the lipid vesicles sold under a variety of trade names including Maalox® and Mylanta®.

As noted, the problem with most present antacids is that although dosage should be less than four hours apart, the duration of activity ends in under an hour. The antacid of the invention contains about the same amounts of base and antiflatulence agents as present antacids but also includes 10–70% by volume lipid vesicles. The addition of the lipid vesicles is the critical step in achieving the requisite duration of residence. Therefore, this extended duration material, which should provide two or more hours of buffering activity, is preferable.

The following examples will assist in illustrating the invention.

EXAMPLE 1

In this Example, Rhesus monkeys were used to show retention of lipid vesicles by the gastric and upper intestinal systems. Paucilamellar lipid vesicles were made using poloxyethylene 9 glycerol monostearate, cholesterol and lidocaine as a charge producing agent. These vesicles were loaded with an aqueous solution of technetium 99, a radioactive ion. The vesicles were made by heating the lipids, blending the heated lipids with an excess of an aqueous solution containing the radioactive ion by syringe mixing, and separating the vesicles. Further details of this procedure are set forth in Example 2 and U.S. Pat. No. 4,911,928. A control solution was made of the technetium 99 in the same carrier without vesicles.

Each solution was gavaged directly into a monkey's stomach. Gamma cameras were placed to record the transit through the gastrointestinal tract and pictures were taken at one hour and one hour and thirty minutes post-dosage. The cameras were focused so they would just show the gastric and upper or proximal intestinal areas.

In the control monkey, the transit of the technetium 99 was so rapid that photographs taken at one hour and one hour and thirty minutes showed no technetium because it already passed through the field of view of the camera. In contrast, the vesicle encapsulated technetium showed greater than ninety percent of the dosage still remain in the stomach at one hour, and at one hour and thirty minutes, approximately sixty percent of the dosage was in the stomach and roughly forty percent was in the proximal small intestine.

Accordingly, it is clear from this data that the lipid vesicles are somehow delayed in transit through the gastric and proximal small intestine systems.

EXAMPLE 2

This Example is confirmation of the testing shown in Example 1. Lipid vesicles were made using the procedures described in U.S. Pat. No. 4,911,928, using polyoxyethylene 2 cetyl ether (Brij 52) as the main lipid. The vesicles used contain calcein dye.

Briefly, the vesicles were made by making a lipophilic phase of the Brij 52, cholesterol, and a quaternary amine to provide a positive charge. The calcein solution formed an aqueous phase. The materials were heated and placed in connected syringes with a stopcock in between, with the lipophilic phase in one syringe and the aqueous phase in the other. The materials were mixed back and forth for approximately two minutes until substantially all the lipid had been converted into large paucilamellar lipid vesicles containing the calcein in their amorphous central cavity.

The lipid vesicles containing the calcein were given to rats by gastric catheter. ACE Wistar rats weighing about 100–125 grams each were fasted for 24 hours before vesicle ingestion and then allowed access to water ad libitum. The first group of animals received a single dose of 0.005 ml of the calcein vesicles, the second 0.01 ml, the third 0.05 ml, the fourth 0.1 ml, and the fifth 0.2 ml. The volume of the total solution was kept constant using phosphate buffered normal saline. The rats were sacrificed at 2, 4 and 6 hours post-ingestion.

The gastric contents were examined by phase contrast microscopy for persistence of intact lipid vesicles and the amount of calcein dye retained in the stomach was determined by photofluorometry. Table 1 shows the results of the testing.

TABLE 1

| Dose/Rat | % Liposome Dye Remaining in Stomach Post Instillation | | |
|---|---|---|---|
| | 2 Hrs | 4 Hrs | 6 Hrs |
| 0.005 ml | 13.25 | 11.25 | 9.0 |
| 0.01 ml | 21.25 | 15.38 | 10.7 |
| 0.05 ml | 25.8 | 12.9 | 7.07 |
| 0.1 ml | 35.4 | 26.2 | 16.2 |
| 0.2 ml | 36.6 | 30.2 | 26.3 |

The 0.01 ml level is approximately equivalent of a teaspoon or 5 ml for a 50 kg person. Therefore, for a larger person, the normal 2–4 teaspoon dosage would be approximated by the 0.05 ml dosage.

This experiment shows that even as much as six hours later, a substantial proportion of the lipid vesicles are retained in the stomach.

EXAMPLE 3

In this Example, the aggregation between vesicles and a base commonly used in antacid preparations is shown.

Nine different vesicle formulations were made. A lipid phase was formed of (1) glycerol monostearate (GMS), (2) cholesterol, (3) a charge producing agent, either ceytl pyridinium chloride (CPC) for a positive charge or oleic acid for a negative charge, and possibly (4) a second surfactant, Tween 60 (polyoxyethylene 20 sorbitan monooleate). All these materials were blended, at about 70° C., to form a lipophilic phase. Two ml of this lipophilic phase was blended with either 1.5 or 2 ml of sesame oil using syringes and then either 12 or 18 ml of an aqueous phase is blended using the syringe method described in Example 2 to form the vesicles. Table 2 shows the proportions for each of the test vesicles.

TABLE 2

| | 1 | 2 | 3 | 4 | 5 | 6 | 7 | 8 | 9 |
|---|---|---|---|---|---|---|---|---|---|
| GMS | 3.9 g | 3.9 g | 4.0 g | 3.2 g | 3.2 g | 3.1 g | 2.9 g | 2.8 g | 3.5 g |
| Cholesterol | 0.85 g | 1.0 g | 0.85 g | 0.9 g | 0.9 g | 0.9 g | 0.9 g | 0.9 g | 0.75 g |
| CPC | 0.23 g | 0.12 g | 0.34 g | | | | | | |
| Tween 60 | | | | 0.85 g | 0.8 g | 0.8 g | 0.8 g | 0.8 g | |
| Oleic Acid | | | | 0.85 g | 0.1 g | 0.1 g | 0.4 g | 0.5 g | 0.75 g |

TABLE 2-continued

|  | 1 | 2 | 3 | 4 | 5 | 6 | 7 | 8 | 9 |
|---|---|---|---|---|---|---|---|---|---|
| Sesame Oil | 1.5 ml | 1.5 ml | 1.5 ml | 2.2 ml | 2.2 ml | 2.2 ml | 2.2 ml | 2.2 ml | 2.2 ml |
| Water | 12 ml | 12 ml | 12 ml | 18 ml | 18 ml | 18 ml | 18 ml | 18 ml | 18 ml |

The vesicles were mixed with Maalox Extra Strength Plus®, an antacid formulation which contains magnesium hydroxide, aluminum hydroxide and simethicone as the active ingredients. The mixtures tested 10%, 25% and 40% by volume vesicles. A control was made by mixing the same volume of water without vesicles with the Maalox. All solutions were divided into two portions; one kept at room temperature, and one kept at 40° C.

After 1 week, all of the samples except the control showed intact lipid vesicles. The negatively charged samples (with oleic acid) showed a slight aggregation, the positively charged (CPC) vesicles showed substantial aggregation, and the water control showed a clear supernatant with all of the solids at the bottom, showing no aggregation. Based on these experiments, it is clear that lipid vesicles will aggregate with the metallic bases in antacids and that the positively charged lipid vesicles are advantageous in promoting aggregation. The combination of the aggregating activity with the extended duration of the vesicles in the gastrointestinal tract is the theorized basis of extended activity.

EXAMPLE 4

In this Example, lipid vesicles were blended with an antacid, Maalox Extra Strength Plus®, and tested to determine whether the acid buffering capacity was degraded. The lipid vesicles were made by blending 1.95 g of glyceryl distearate, 1.65 g of polyoxytheylene stearyl alcohol, 0.4 g cholesterol, and 0.025 g dimethyl-distearyl ammonium (Varisoft), and adding 5 ml of sesame oil to make a lipophilic phase, and placing the heated lipid mixture in a 60 ml syringe. Water (40.5 ml) heated at 65° C. was placed in another 60 ml syringe and the two syringes were joined with a steel stopcock. The materials pushed from one syringe to another for approximately two minutes until lipid vesicles were formed.

A control was made by taking 10 ml of Maalox Extra Strength Plus® and adding 70 ml of water. A magnetic stirring bar was placed in the Maalox Extra Strength Plus solution and 60 ml of 1N HCl acid was added and stirred at 300 rpm for fifteen minutes. The resulting pH was 1.56. Following this, 0.5N NaOH solution was added dropwise while stirring until the pH was 3.5. The amount of added NaOH was 8 ml.

The sample was made by taking 5 ml of Maalox Extra Strength Plus, 5 ml of the vesicles prepared as described above, and adding 70 ml of water.

A magnetic stirring bar was then placed in the Maalox/lipid vesicle suspension. Thirty ml of 1N HCl was added and stirred for fifteen minutes. The pH was 1.99. Again, 0.5N NaOH was added dropwise until the pH was 3.5. This required 3.4 ml of NaOH for neutralization.

The calculated acid neutralizing capacity of the Maalox itself was 56 mEq/10 ml. When the 10 ml of the lipid vesicle/Maalox solution was tested, it showed 28.3 mEq/10 ml capacity or 56.6 mEq/10 ml base. This is within the margin of error of the test, showing that the addition of the lipid vesicles does not modify the acid neutralizing capacity of the base.

EXAMPLE 5

In this Example, classic multilamellar liposomes were made to see how they reacted to an acidic solution. Hydrogenated phosphatidylcholine (Natterman) was made into lipid vesicles using the Bangham method. Briefly, the phosphatidylcholine was dissolved in 2:1 chloroform/ethanol, and the solvent, was evaporated, and the lipid was rehydrated and formed into vesicles with an aqueous solution.

The multilamellar vesicles were placed in 0.25M and 0.5M HCl solutions. Within an hour, the samples had deteriorated to a point that the experiment could not be continued. This is in contrast to using lipid vesicles such as those described in the previous Examples which are stable in these solutions.

The foregoing examples are meant to be illustrative and are not intended to be limiting in any way. The scope of the invention is not defined by these examples but rather by the following claims.

What is claimed is:

1. An antacid product having extended residence and duration in the gastric and upper intestinal systems comprising mixture of non-phospholipid lipid vesicles and an effective amount of a particulate base in a substantially aqueous solution, said lipid vesicles comprising 10–70% by weight of said product, and wherein said non-phospholipid is selected from the group consisting of:

diethanolamides having the formula $$(HOCH_2—CH_2)_2NCO—R_3$$

where $R_3$ is a radical of caprylic, lauric, myristic or linoleic acids;

long chain acyl hexosamides having the formula $$R_4—NHCO—(CH_2)_b—CH_3$$

where b ranges from 10–18 and $R_4$ is a radical of a sugar molecule selected from a group consisting of glucosamine, galactosamine, and N-methylglucamine; and long chain acyl amino acid amides having the formula $$R_5—CH(COOH)—NHCO—(CH_2)_c—CH_3$$

where c ranges from 10–18 and $R_5$ is a radical of an amino acid side chain;

long chain acyl amides having the formula $$HOOC—(CH_2)_d—N(CH_3)—(CH_2)_3—NHCO—R_6$$

where $R_6$ is an acyl chain having 12–20 carbon and not more than two unsaturations, and d ranges from 1–3;

glycerol monostearate;

polyoxyethylene fatty esters having the formula $$R_1—COO(C_2H_4O)_nH$$

where $R_1$ is a radical of lauric, myristic, cetyl, stearic, or oleic acid and n=2–10;

polyoxyethylene fatty acid ethers, having the formula $$R_2\text{—}CO(C_2H_4O)_m H$$

where $R_2$ is a radical of lauric, myristic, or cetyl acids, single or double unsaturated octadecyl acids, or double unsaturated eicodienoic acids and m ranges from 2–4;

polyoxyethylene (20) sorbitan mono- or trioleate;

polyoxyethylene glyceryl monostearate with 1–10 polyoxyethylene groups;

betaines; and sarcosinamides.

2. The product of claim 1 wherein said base is selected from the group consisting of metal hydroxides, metal hydrosilicates, metal carbonates and bicarbonates, and mixtures thereof.

3. The product of claim 2 wherein said metal is selected from the group consisting of Na, Ca, Al and Mg, and mixtures thereof.

4. The product of claim 1 further comprising an antiflatulence agent.

5. The product of claim 4 wherein said antiflatulence agent comprises a silicone oil.

6. The product of claim 5 wherein said silicone oil comprises simethicone.

7. The product of claim 1 wherein said lipid vesicles further comprise a charge-producing agent.

8. The product of claim 7 wherein said charge producing agent is a positive charge producing agent.

9. The product of claim 8 wherein said positive charge producing agent is selected from the group consisting of long chain amines, long chain pyridinium compounds, quaternary ammonium compounds, and mixtures thereof.

10. The product of claim 9 wherein said positive charge producing agent comprises cetyl pyridinium chloride.

11. The product of claim 7 wherein said charge producing agent is a negative charge producing agent selected from the group consisting of dicetyl phosphate, cetyl sulfate, phosphatidic acid, phosphatidyl serine, oleic acid, palmitic acid, and mixtures thereof.

12. The product of claim 1 wherein said lipid vesicle further comprises a sterol.

13. The product of claim 11 wherein said sterol is selected from the group consisting of cholesterol, phytosterol, hydrocortisone, and mixtures thereof.

14. The product of claim 1 wherein said antacid product is dried.

15. A method of ameliorating acid build up in the gastric and upper intestinal tracts comprising, administering to a human host an effective amount of an antacid product comprising an effective amount of a mixture of non-phospholipid lipid vesicles and an effective amount of a particulate base in a substantially aqueous solution, said lipid vesicles comprising 10–70% by weight of said product, and wherein said non-phospholipid is selected from the group consisting of:

diethanolamides having the formula $$(HOCH_2\text{—}CH_2)_2 NCO\text{—}R_3$$

where $R_3$ is a radical of caprylic, lauric, myristic or linoleic acids;

long chain acyl hexosamides having the formula $$R_4\text{—}NHCO\text{—}(CH_2)_b\text{—}CH_3$$

where b ranges from 10–18 and $R_4$ is a radical of a sugar molecule selected from a group consisting of glucosamine, galactosamine, and N-methylglucamine; and long chain acyl amino acid amides having the formula $$R_5\text{—}CH(COOH)\text{—}NHCO\text{—}(CH2)_c\text{—}CH_3$$

where c ranges from 10–18 and R5 is a radical of an amino acid side chain;

long chain acyl amides having the formula $$HOOC\text{—}(CH_2)_d\text{—}N(CH_3)\text{—}(CH_2)_3\text{—}NHCO\text{—}NHCO\text{—}R_6$$

where $R_6$ is an acyl chain having 12–20 carbons and not more than two unsaturations, and d ranges from 1–3;

glycerol monostearate;

polyoxyethylene fatty esters having the formula $$R_1\text{—}COO(C_2H_4O)_n H$$

where $R_1$ is a radical of lauric, myristic, cetyl, stearic, or oleic acid and n=2–10;

polyoxyethylene fatty acid ethers, having the formula $$R_2\text{—}CO(C_2H_4O)_m H$$

where $R_2$ is a radical of lauric, myristic, or cetyl acids, single or double unsaturated octadecyl acids, or double unsaturated eicodienoic acids and m ranges from 2–4;

polyoxyethylene (20) sorbitan mono- or trioleate;

polyoxyethylene glyceryl monostearate with 1–10 polyoxyethylene groups;

betaines; and sarcosinamides.

16. The method of claim 15 wherein said base is selected from the group consisting of metal hydroxides, metal hydrosilicates, metal carbonates and bicarbonates, and mixtures thereof.

17. The method of claim 16 wherein said metal is selected from the group consisting of Na, Ca, Al and Mg, and mixtures thereof.

18. The method of claim 15 wherein said antacid product further comprises an antiflatulence agent.

19. The method of claim 18 wherein said antiflatulence agent comprises a silicone oil.

20. The method of claim 19 wherein said silicone oil comprises simethicone.

21. The method of claim 15 wherein said lipid vesicles further comprise a charge-producing agent.

22. The method of claim 21 wherein said charge producing agent is a positive charge producing agent.

23. The method of claim 22 wherein said positive charge producing agent is selected from the group consisting of long chain amines, long chain pyridinium compounds, quaternary ammonium compounds, and mixtures thereof.

24. The method of claim 23 wherein said positive charge producing agent comprises cetyl pyridinium chloride.

25. The method of claim 21 wherein said charge producing agent is a negative charge producing agent selected from the group consisting of dicetyl phosphate, cetyl sulfate, phosphatidic acid, phosphatidyl serine, oleic acid, palmitic acid, and mixtures thereof.

26. The method of claim 15 wherein said lipid vesicle further comprises a sterol.

27. The method of claim 25 wherein said sterol is selected from the group consisting of cholesterol, phytosterol, hydrocortisone, and mixtures thereof.

28. The method of claim 15 wherein said antacid product is dried.

29. An antacid product having extended residence and duration in the gastric and upper intestinal systems comprising a mixture of non-phospholipid lipid vesicles and an effective amount of a particulate base in a substantially aqueous solution, said lipid vesicles comprising 10–70% by weight of said product, and wherein said non-phospholipid is selected from the group consisting of:

a blend of two distinct lipids, a primary lipid and a secondary lipid, wherein the primary lipid, which forms the greatest proportion by weight of any lipid is 50% or higher by weight of lipid in the vesicle, is selected from the group consisting of $C_{12}$–$C_{18}$ fatty alcohols, $C_{12}$–$C_{18}$ glycol monoesters, $C_{12}$–$C_{18}$ glyceryl mono- and diesters, and mixtures thereof; and wherein the secondary lipid must be present in an amount sufficient to allow formation of the lipid vesicles, and is selected from the group consisting of quaternary dimethyldiacyl amines, polyoxyethylene acyl alcohols, polyglycerols, sorbitan fatty acid esters, fatty acids and their salts, and mixtures thereof.

30. A method of ameliorating acid build up in the gastric and upper intestinal tracts comprising, administering to a human host an effective amount of an antacid product comprising an effective amount of a mixture of non-phospholipid lipid vesicles and an effective amount of a particulate base in a substantially aqueous solution, said lipid vesicles comprising 10–70% by weight of said product, and wherein said non-phospholipid is selected from the group consisting of:

a blend of two distinct lipids, a primary lipid and a secondary lipid, wherein the primary lipid, which forms the greatest proportion by weight of any lipid is 50% or higher by weight of lipid in the vesicle, is selected from the group consisting of $C_{12}$–$C_{18}$ fatty alcohols, $C_{12}$–$C_{18}$ glycol monoesters, $C_{12}$–$C_{18}$ glyceryl mono- and diesters, and mixtures thereof; and wherein the secondary lipid must be present in an amount sufficient to allow formation of the lipid vesicles, and is selected from the group consisting of quaternary dimethyldiacyl amines, polyoxyethylene acyl alcohols, polyglycerols, sorbitan fatty acid esters, fatty acids and their salts, and mixtures thereof.

\* \* \* \* \*